United States Patent
Kuhn

(10) Patent No.: US 12,167,857 B2
(45) Date of Patent: *Dec. 17, 2024

(54) CLAMP DEVICE FOR HEMOSTASIS OR CLOSURE OF TISSUE AND MEDICAL INSTRUMENT FOR HEMOSTASIS OR CLOSURE OF TISSUE

(71) Applicant: MICRO-TECH (NANJING) CO., LTD., Jiangsu (CN)

(72) Inventor: Daniel Kuhn, Düsseldorf (DE)

(73) Assignee: MICRO-TECH (NANJING) CO., LTD., Jiangsu (CN)

( * ) Notice: Subject to any disclaimer, the term of this patent is extended or adjusted under 35 U.S.C. 154(b) by 605 days.

This patent is subject to a terminal disclaimer.

(21) Appl. No.: 17/599,650

(22) PCT Filed: Apr. 17, 2020

(86) PCT No.: PCT/CN2020/085337
§ 371 (c)(1),
(2) Date: Sep. 29, 2021

(87) PCT Pub. No.: WO2020/211838
PCT Pub. Date: Oct. 22, 2020

(65) Prior Publication Data
US 2022/0202422 A1    Jun. 30, 2022

(30) Foreign Application Priority Data

Apr. 17, 2019  (EP) .................................. 19169940
Apr. 17, 2019  (EP) .................................. 19169946
Jul. 10, 2019   (EP) .................................. 19185556

(51) Int. Cl.
*A61B 17/122*  (2006.01)
*A61B 17/128*  (2006.01)
*A61B 17/12*   (2006.01)

(52) U.S. Cl.
CPC ........ *A61B 17/122* (2013.01); *A61B 17/1285* (2013.01); *A61B 2017/12004* (2013.01)

(58) Field of Classification Search
CPC . A61B 17/122; A61B 17/128; A61B 17/1285; A61B 17/29; A61B 2017/0034;
(Continued)

(56) References Cited

U.S. PATENT DOCUMENTS 7,094,245 B2 * 8/2006 Adams ................... A61B 90/03
                                                            606/139
7,879,052 B2 * 2/2011 Adams ................. A61B 17/122
                                                            606/157
(Continued)

FOREIGN PATENT DOCUMENTS

CN    102626335 A    8/2012
CN    102090910 B    12/2012
(Continued)

OTHER PUBLICATIONS

European Search Report and Opinion with regard to EP19185556.8 completed Jan. 7, 2020.
(Continued)

*Primary Examiner* — Ryan J. Severson
(74) *Attorney, Agent, or Firm* — BCF LLP

(57) ABSTRACT

A clamp device for hemostasis or closure of tissue, including clamp housing and at least two clamp arms, wherein clamp arms can be coupled to distal end of control wire of medical instrument to stop bleeding of blood vessel, clamp device can be actuated to open and close clamp arms, which are coupled to each other or can be coupled at proximal ends, clamp arms is provided with guide groove, and guide grooves of clamp arms partially overlap each other, and guide pin attached to clamp housing, and extending in overlapping part of guide grooves and passing therethrough,
(Continued)

so that by means of fitting of guide pin and guide grooves, movement of pivot axis is converted into closing movement of clamp arms or opening movement of clamp arms about pivot axis, holding hole being provided on each of clamp arm, holding hole extending from side thereof into guide groove.

24 Claims, 10 Drawing Sheets

(58) Field of Classification Search
CPC .......... A61B 2017/00477; A61B 2017/00862; A61B 2017/12004; A61B 2017/2936
See application file for complete search history.

(56) References Cited

U.S. PATENT DOCUMENTS

| | | | |
|---|---|---|---|
| 8,062,311 B2 * | 11/2011 | Litscher | A61B 17/122 606/143 |
| 8,070,760 B2 | 12/2011 | Fujita | A61B 17/1227 606/151 |
| 8,858,588 B2 * | 10/2014 | Sigmon, Jr. | A61B 17/08 606/205 |
| 8,915,837 B2 * | 12/2014 | Wells | A61B 17/122 606/139 |
| 9,084,604 B2 * | 7/2015 | Litscher | A61B 17/122 |
| 9,510,836 B2 * | 12/2016 | Zhu | A61B 17/1227 |
| 9,795,390 B2 * | 10/2017 | Jin | A61B 17/1285 |
| 10,172,623 B2 * | 1/2019 | Adams | A61B 17/1285 |
| 10,470,777 B2 * | 11/2019 | Litscher | A61B 17/1285 |
| 10,799,358 B2 * | 10/2020 | Erickson | A61B 17/295 |
| 10,820,904 B2 * | 11/2020 | Ryan | A61B 17/1285 |
| 11,020,125 B2 * | 6/2021 | Randhawa | A61B 17/122 |
| 11,045,194 B2 * | 6/2021 | King | A61B 17/128 |
| 11,160,558 B2 * | 11/2021 | Lehtinen | A61B 17/10 |
| 11,857,213 B2 * | 1/2024 | Nelson | A61B 17/282 |
| 2003/0069592 A1 | 4/2003 | Adams et al. | |
| 2005/0107809 A1 * | 5/2005 | Litscher | A61B 17/1285 606/142 |
| 2005/0182426 A1 * | 8/2005 | Adams | A61B 17/083 606/213 |
| 2009/0105533 A1 | 4/2009 | Fujita | |
| 2012/0065647 A1 * | 3/2012 | Litscher | A61B 17/1285 606/143 |
| 2012/0071898 A1 | 3/2012 | Wells et al. | |
| 2012/0089176 A1 * | 4/2012 | Sigmon, Jr. | A61B 17/10 606/205 |
| 2014/0088616 A1 | 3/2014 | Clerc et al. | |
| 2014/0171973 A1 | 6/2014 | Zhu | |
| 2015/0282813 A1 | 10/2015 | Litscher et al. | |
| 2016/0128698 A1 * | 5/2016 | Adams | A61B 17/083 606/142 |
| 2016/0367258 A1 * | 12/2016 | Jin | A61B 17/1285 |
| 2018/0049745 A1 | 2/2018 | Randhawa et al. | |
| 2018/0078262 A1 | 3/2018 | Lehtinen et al. | |
| 2018/0085122 A1 | 3/2018 | Ryan et al. | |
| 2018/0153552 A1 | 6/2018 | King et al. | |
| 2019/0053904 A1 | 2/2019 | Erickson et al. | |
| 2019/0090883 A1 * | 3/2019 | Adams | A61B 17/1227 |
| 2022/0160366 A1 * | 5/2022 | Kuhn | A61B 17/122 |
| 2022/0167990 A1 * | 6/2022 | Kuhn | A61B 17/122 |
| 2022/0202422 A1 * | 6/2022 | Kuhn | A61B 17/122 |

FOREIGN PATENT DOCUMENTS

| | | |
|---|---|---|
| CN | 202699217 U | 1/2013 |
| CN | 202699218 U | 1/2013 |
| CN | 103200883 A | 7/2013 |
| CN | 102626335 B | 4/2014 |
| CN | 103989500 A | 8/2014 |
| CN | 203828993 U | 9/2014 |
| CN | 105935304 A | 9/2016 |
| CN | 206239447 U | 6/2017 |
| CN | 107115130 A | 9/2017 |
| CN | 206482631 U | 9/2017 |
| CN | 107684448 A | 2/2018 |
| CN | 108635007 A | 10/2018 |
| CN | 109009310 A | 12/2018 |
| CN | 109199515 A | 1/2019 |
| CN | 208435704 U | 1/2019 |
| CN | 109480950 A | 3/2019 |
| CN | 109805977 A | 5/2019 |
| CN | 209884245 U | 1/2020 |
| EP | 1328199 A1 | 7/2003 |
| EP | 1829489 A1 | 9/2007 |
| EP | 2371303 A1 | 10/2011 |
| EP | 2380509 A2 | 10/2011 |
| EP | 3053532 A1 | 8/2016 |
| EP | 3081174 A1 | 10/2016 |
| EP | 1328199 B1 | 6/2018 |
| WO | 95/11620 A2 | 5/1995 |
| WO | 2008/070486 A2 | 6/2008 |
| WO | 2011/022246 A1 | 2/2011 |
| WO | 2012/051191 A2 | 4/2012 |
| WO | 2018/235402 A1 | 12/2018 |

OTHER PUBLICATIONS

European Search Report and Opinion with regard to EP19169940.4 completed Dec. 3, 2019.
European Search Report and Opinion with regard to EP19169946.1 completed Oct. 15, 2019.
Insternational Search Report (including Translation) and Writte Opinion with regard to PCT/CN2020/085337 completed Jun. 23, 2020.
Partial European Search Report with regard to EP19169940 completed Oct. 8, 2019.
English Abstract for CN108635007 retrieved on Espacenet on Sep. 20, 2021.
English Abstract for CN107684448 retrieved on Espacenet on Sep. 22, 2021.
English Abstract for CN105935304 retrieved on Espacenet on Jul. 13, 2021.
English Abstract for CN102090910 retrieved on Espacenet on Sep. 22, 2021.
English Abstract for CN102626335 retrieved on Espacenet on Jul. 13, 2021.
English Abstract for CN202699217 retrieved on Espacenet on Sep. 27, 2021.
English Abstract for CN202699218 retrieved on Espacenet on Sep. 27, 2021.
English Abstract for CN208435704 retrieved on Espacenet on Jul. 13, 2021.
English Abstract for CN206482631 retrieved on Espacenet on Sep. 27, 2021.
English Abstract for CN109199515 retrieved on Espacenet on Sep. 27, 2021.
English Abstract for CN103989500 retrieved on Espacenet on Jul. 13, 2021.
English Abstract for CN206239447 retrieved on Espacenet on Sep. 27, 2021.
English Abstract for CN203828993 retrieved on Espacenet on Jul. 13, 2021.
English Abstract for CN109480950 retrieved on Espacenet on Jul. 13, 2021.
International Search Report (including English Translation) and Written Opinion with regard to PCT/CN2020/084280 mailed Jun. 23, 2020.
English Abstract for CN109805977 retrieved on Espacenet on Jul. 13, 2021.
English Abstract for CN209884245 retrieved on Espacenet on Jul. 13, 2021.
English Abstract for CN107115130 retrieved on Espacenet on Jul. 13, 2021.
English Abstract for CN103200883 retrieved on Espacenet on Jul. 13, 2021.

(56) References Cited

OTHER PUBLICATIONS

International Search Report (including English Translation) and Written Opinion with regard to PCT/CN2020/084497 mailed Jun. 29, 2020.
English Abstract for CN109009310 retrieved on Espacenet on Jul. 13, 2021.

* cited by examiner

CLAMP DEVICE FOR HEMOSTASIS OR CLOSURE OF TISSUE AND MEDICAL INSTRUMENT FOR HEMOSTASIS OR CLOSURE OF TISSUE

CROSS-REFERENCE TO RELATED APPLICATIONS

The present application is a National Stage of International Application No. PCT/CN2020/085337, filed on Apr. 17, 2020, which claims the priority to the European patent application with the filing number 19169940.4 filed on Apr. 17, 2019 with the European Patent Office and entitled "Medical Device for Causing Hemostasis of Blood Vessel", the European patent application with the filing number 19169946.1 filed on Apr. 17, 2019 with the European Patent Office and entitled "Medical Device for Causing Hemostasis of Blood Vessel", and the European patent application with the filing number 19185556.8 filed on Jul. 10, 2019 with the European Patent Office and entitled "Medical Device for Causing Hemostasis of Blood Vessel", the contents of each of which are incorporated herein by reference in its entirety.

TECHNICAL FIELD

The present disclosure relates to the technical field of medical devices, in particular to a clamp device for tissue hemostasis or closure and a medical device for tissue hemostasis or closure.

BACKGROUND ART

Medical devices of this kind are known in the prior art, for example from EP1328199B1 and in particular used to treat gastrointestinal bleedings. Specifically, such devices are used to set clamps or clips to pinch a bleeding vessel applying sufficient constrictive force to the blood vessel so as to limit or interrupt blood flow passing therethrough.

The medical device known from EP1328199B1 includes a handle and a sheath, which is attached to the handle. A control wire extends through the sheath and can be actuated by an actuator, which is coupled to a proximal end of the control wire so as to reversibly move the control wire in distal and proximal directions. The medical device further includes a clamp device including a sleeve provided on a distal end of the sheath and a clip with two clamp arms, and the clamp arms are coupled to a distal end of the control wire by means of a J-hook. The clamp arms cooperate with the sleeve in such a way, that the clamp arms engage a front edge of the sleeve to be elastically deformed inwardly, thus being closed, when the control wire is pulled in a proximal direction, whereas the clamp arms are distally pushed out of the sleeve and automatically reopen due to their elastic restoring force, when the control wire is pushed in the distal direction. Since the clamp device can be repeatedly opened and closed, setting of the clamp device is possible in an easy way.

Once the clamp device is positioned correctly, the clamp device with the clamp arms and the sleeve can be disconnected from the rest of the medical device. In order to do so the control wire is further pulled back, when the clamp device is completely closed, so that the J-hooks break and thus the connection between the clamp arms and the control wire is interrupted. Moreover, by further pulling back the control wire, a retainer which connects the control wire with the sleeve is actuated, in order to disconnect the retainer from the sleeve and thus the control wire from the sleeve.

SUMMARY

In order to solve at least one technical problem in the prior art, the objects of the present disclosure include providing a clamp device and a medical device of the above mentioned kind that are easy to operate as well as easy to manufacture and assemble, and that operate in a reliable manner.

According to an embodiment of the present disclosure, a clamp device for tissue hemostasis or closure is provided, including a clamp housing, in particular with a clamp base, which is optionally in the form of a sleeve, and at least two clamp arms, wherein the clamp arms are able to be coupled to a distal end of a control wire of a medical device, and wherein the clamp device is actuable to open and close the clamp arms, wherein the clamp device includes exactly two clamp arms, which are provided as separate elements, wherein the clamp arms are coupled or are able to be coupled at their proximal ends to each other such that the clamp arms can be rotated around a common pivot axis, each clamp arm being provided with a guide groove and the guide grooves of the clamp arms partially overlapping each other, and a guide pin, which is attached to the clamp housing and extends through the guide grooves in the overlapping parts thereof, so that by the engagement of the guide pin and the guide grooves a movement of the pivot axis is translated into a closing movement of the clamp arms or into an opening movement of the clamp arms around the pivot axis.

Besides, an embodiment of the present disclosure further provides a clamp device for tissue hemostasis or closure, including a clamp housing and at least two clamp arms, wherein the clamp arms are coupled or able to be coupled to a distal end of a control wire of a medical device, and wherein the clamp device is actuable to open and to close the clamp arms, and wherein the clamp device includes exactly two clamp arms, each clamp arm defines at its distal end a grasping section in order to grasp a tissue when the clamp device is released inside the body of a patient.

Besides, an embodiment of the present disclosure further provides a medical device for tissue hemostasis or closure.

The above objects at least may be achieved by a clamp device mentioned at the beginning in that holding noses are provided on the clamp arms, the holding noses extending into the guide grooves from a lateral side thereof and being designed in such a way, that they allow the guide pin to pass them to reach the distal ends of the guide grooves but prevent passing of the guide pin in an opposite direction. Accordingly, the clamp arms are separate elements/components that are not directly connected to one another. Instead, they are each coupled or able to be coupled to a control wire of a medical device. Moreover, they are coupled by the engagement of the guide pin and the guide grooves to the clamp housing in such a way that an axial movement of the common pivot axis is translated into an opening/closing movement of the clamp arms.

The guide pin can be captured in the distal ends of the guide grooves by means of the holding noses, thus locking the clamp arms to the clamp housing, when the clamp arms are fully closed and should remain in the patient's body. In particular, it is may be provided that the holding noses deform elastically, when the guide pin passes them. In this way further locking elements are no more necessary and a very reliable and stable locking of the clamp arms is obtained.

According to an optional embodiment of the present disclosure, each clamp arm may include exactly one holding nose extending into the respective guide groove. This means, that only on one lateral side of the guide groove, a holding nose extending into the latter is formed.

In concrete terms, the clamp arms may be coupled at their proximal ends to a pivot pin defining the common pivot axis. Such a pivot pin may engage through corresponding through-holes formed in a proximal end section of the clamp arms. It is conceivable that the clamp device is provided as a spare-part for use with a reloadable medical device allowing the insertion of the clamp device into the body of a patient. In that case, a pivot pin can be fixedly attached to the distal end of a control wire, which means that the pivot pin is coupled to the clamp arms when the clamp device is connected to the reloadable medical device for inserting the clamp device into the patient's body. Generally, it is also possible that such a pivot pin is fixedly connected to proximal tail ends of the clamp arms and is coupled to the distal end of a control wire when the clamp device is connected to a medical device for insertion into the body of a patient.

According to an optional embodiment of the present disclosure, the guide grooves have a straight, axially extending distal end section, in which the guide pin can move without incurring rotation of the clamp arms and the holding noses extend into the straight distal end sections, and/or recesses, in particular formed as through-openings, are formed in the clamp arms laterally to the guide grooves in proximity to the holding noses such that the holding noses can deform elastically to allow the guide pin to pass the holding noses and reach its distal end position in the guide grooves. In other words, the straight and axially extending distal end section of the guide grooves results in a movement of the clamp arms without rotation when the pivot pin is pulled in proximal direction by means of the control wire. Recesses, which are in particular arranged at the same axial position as the holding noses and directly laterally to the holding noses, lead to an increased elastic deformation of the holding noses. The recesses, which in particular are formed as through-openings, may have a triangular shape, one corner of which is directed to the guide groove.

The guide pin may be held between two bearing arms of the clamp housing extending in the distal direction from a clamp base, which is in particular formed as a sleeve, optionally at the free end sections of the bearing arms.

The objects further at least may be achieved by another clamp device mentioned at the beginning in that holding humps are provided on the clamp arms, the holding humps extending into the guide grooves from lateral sides thereof, and in that the guide pin includes a radially deformable middle section extending through the guide grooves allowing the guide pin to pass the holding humps.

In other words, it is provided that the guide pin is radially deformable, in particular radially squeezable, to allow the guide pin to pass the holding humps extending into the guide grooves and thus locally reducing the width of the guide grooves forming an obstacle. Consequently, it is not intended that the holding humps deform significantly but that the guide pin is pressed by the contact with the holding humps when passing them.

According to an optional embodiment, the guide pin is, at least in its middle section extending through the guide grooves of the clamp arms, in particular over its entire length, tubular shaped having an inner opening. Such a tubular shape increases the flexibility and the ability of the guide pin to be squeezed radially elastically.

Optionally, at least one slit, in particular at least one through-slit extending from the outer surface of the guide pin until the inner opening, is formed in the middle section of the guide pin. Such a slit or a plurality of slits decrease the stiffness of the guide pin and increase its ability to be elastically deformed.

In a further elaboration of this embodiment, a plurality of slits may extend in the longitudinal direction of the guide pin and/or are spaced over the entire circumference of the guide pin. By means of such a plurality of slits which extend in particular at least over the middle section of the guide pin, an elastic radial deformation for passing the holding humps is realized.

It may also be provided, that at least one slit is formed helically over the middle section of the guide pin. Such a helically formed slit, in particular when formed as a through-slit extending until the inner opening of the guide pin, increases the flexibility of the middle section of the guide pin. In otherwords, in case of a through-slit, the middle section of the guide pin is formed like a spiral spring which can easily be deformed and in particular squeezed radially when the guide pin has to pass the holding humps extending into the guide grooves.

Optionally, the guide grooves have a straight, axially extending distal end section, in which the guide pin can move without incurring rotation of the clamp arms and the holding humps extend through the distal end sections, wherein, in particular, each clamp arm has two holding humps, one holding hump of which extends from each lateral side of the guide groove.

The clamp arms are coupled at their proximal ends to a pivot pin defining the common pivot axis. Such a pivot pin may engage through corresponding through-holes formed in the proximal end section of the clamp arms. It is conceivable that the clamp device is provided as a spare-part for use with a reloadable medical device allowing the insertion of the clamp device into the body of a patient. In that case, a pivot pin can be fixedly attached to the distal end of a control wire, which means that the pivot pin is coupled to the clamp arms when the clamp device is connected to the reloadable medical device for inserting the clamp device into the patient's body. Generally, it is also possible that such a pivot pin is fixedly connected to the proximal tail ends of the clamp arms and is coupled to the distal end of a control wire when the clamp device is connected to a medical device for insertion into the body of a patient.

The guide pin may be held between two bearing arms of the clamp housing extending in the distal direction from a clamp base, which is in particular formed as a sleeve, optionally at the free end sections of the bearing arms.

The guide pin may be held between the bearing arms extending in the distal direction from a clamp base, which is in particular formed as a sleeve, optionally at the free end sections of the two bearing arms of the clamp housing.

The object at least further may be achieved by another clamp device mentioned at the beginning in that each clamp arm includes two barbs arranged on laterally opposite sides of the clamp arm in the grasping section wherein the barbs are formed such that each barb points in the direction of a corresponding, opposite barb of the other clamp arm.

In other words, barbs extending towards the other clamp arm are provided with the consequence that the grasping of the tissue is improved and the risk of an unintended release from the tissue is minimized, when the clamp arms are closed clamping tissue between them.

Optionally, a clamping contour is provided at each barb at its end pointing to the corresponding, opposite barb of the other clamp arm. In concrete terms, the clamping contour of each barb is complementary to the clamping contour of the corresponding, opposite barb of the other clamp arm. The clamping contour of at least one barb may include a V-shaped protrusion, wherein the corresponding opposite barb of the other clamp arm has a complementary V-shaped recess. Such a clamping contour further increases the probability that a clamp device fixed inside the body of a patient remains there so that the safety of fixation is improved. A clamping contour of a barb being complementary to the clamping contour of the corresponding barb reduces the risk of damaging blood vessels. In particular, when the clamp arms are fully closed, the corresponding barbs of the clamp arms are not in direct contact, but a distance remains between them.

According to an optional embodiment, each clamp arm has one barb, the clamping contour of which includes a V-shaped protrusion, and one barb, the clamping contour of which includes a V-shaped recess. Optionally, the corners of the V-shaped protrusion(s) and/or the corners of the V-shaped recess(es) are round chamfers. By means of such rounded corners, sharp edges can be avoided and the risk of damaging blood vessels is minimized.

Furthermore, the barbs may optionally be arranged in the most distal end of the grasping section and/or notches, in particular rounded notches, may be formed in the clamp arms adjacent to the barbs. The provision of notches adjacent to the barbs reduces peaks in stresses due to a sharp changing cross section of the clamp arms.

Each clamp arm may be bent inwardly towards the opposite clamp arm at its lateral edges at least over a part of the grasping section, in particular over the entire grasping section. Such a form increases the mechanical stability of the clamp arms and allows a higher clamping force to clamp tissue.

Optionally, the distal end of the grasping section of each clamp arm is bent inwards towards the other clamp arm. In a further elaboration of this embodiment, an engagement contour is formed at the distal end of each clamp arm, wherein the engagement contours of the clamp arms are complementary to each other so that they can engage with each other when the clamp arms are closed. In concrete terms, the engagement contours of the clamp arms may include a corrugated profile, in particular a sinusoidal profile or a zigzag profile.

At least one clamp arm, in particular both clamp arms may include a through-opening formed in the grasping section, in particular extending in the longitudinal direction of the clamp arm. Such a through-opening allows tissue clamped between the clamp arms to expand and therefore increases the safety of the fixation of the clamp device in the body of a patient.

The above clamp device may be provided with clamp arms as separate elements, wherein the clamp arms are coupled or are able to be coupled at their proximal end to each other such that the clamp arms can be rotated around a common pivot axis, each clamp arm being provided with a guide groove and the guide grooves partially overlapping each other. Furthermore, the clamp device may further include a guide pin which is attached to the clamp housing and extends through the guide grooves in the overlapping parts thereof, so that by the engagement of the guide pin and the guide grooves a movement of the guide pin is translated into a closing movement of the clamp arms or into an opening movement of the clamp arms around the pivot axis.

The clamp devices according to the present disclosure may be designed such that the clamp arms are coupled at their proximal ends to a pivot pin defining the common pivot axis.

The object is also achieved by a medical device for tissue hemostasis or closure, the medical device including:
a handle;
a sheath device, which is attached to the handle;
a clamp device according to the present disclosure, as described above;
a control wire extending through the sheath device and reversibly moveable in the distal and proximal directions; and
an actuator coupled to the proximal end of the control wire and being actuable to reversibly move the control wire in distal and proximal directions;
wherein the clamp arms are each coupled to the distal end of the control wire and wherein the clamp device is actuable to open and close the clamp arms by a movement of the control wire such that a movement of the control wire in the proximal direction is translated into a closing movement of the clamp arms and a movement of the control wire in the distal direction is translated into an opening movement of the clamp arms.

Optionally, the clamp arms are coupled at their proximal ends to a pivot pin and are rotatable relative to the pivot pin around a common pivot axis defined by the pivot pin, wherein the distal end of the control wire is coupled to the pivot pin, so that the clamp arms are coupled to the distal end of the control wire via the pivot pin. Accordingly, the clamp arms are separate elements/components that are not directly connected to one another. Instead, they are each coupled to the control wire by the engagement with the pivot pin. This pivot pin defines a common pivot axis around which the clamp arms are rotatable relative to each other.

According to an optional embodiment, the pivot pin extends through a corresponding through-hole provided in a coupling head formed at the distal end section of the control wire and an exit-passage which extends into the through-hole, is provided in the distal end of the coupling head, through which after closing the clamp arms the control wire can be pulled out of engagement from the pivot pin and thus, from the clamp arms, spreading apart the distal end portions of the coupling head on the opposite sides of the exit-passage without breaking the distal end portions by means of a proximal movement of the control wire in order to uncouple the control wire from the clamp arms.

According to this embodiment, the clamp arms are directly coupled to the control wire, thus omitting the necessity to provide for a separate coupling element for example in the form of J-hook. Specifically, the control wire is provided at its distal end section with a pivot pin, which engages corresponding through-holes provided in the proximal end sections of the clamp arms.

The through-holes are open to the distal end of the coupling head. Specifically, exit-passages are provided which are designed such that they are small enough, so that the pivot pin cannot fall out of the coupling head unintentionally, but can be intentionally pulled out of the through-holes through the exit-passages by exerting a sufficiently high tensile force to the control wire, so that the end portions of the coupling head on opposite sides of the exit-passages are spread apart and thus deformed, without breaking. For example, the exit-passages may be formed by slits in the end portions of the coupling head. According to a further embodiment of the present disclosure, the distal end portions of the coupling head are elastically or plastically deformed, when they are spread apart. In any way, the arrangement is such that the end portions of the coupling heads do not break in order to avoid that parts remain freely in the body of a patient.

According to a further embodiment, the pivot pin extends through corresponding through-holes provided in the proximal end section of the clamp arms, wherein exit-passages are provided in the tail ends of the clamp arms, through which, after closing the clamp arms, the pivot pin can be pulled out of engagement from the through-holes of the clamp arms and from the clamp arms, spreading apart the tail end sections of the clamp arms on the opposite sides of the exit-passages without breaking them by a proximal movement of the control wire in order to uncouple the control wire from the clamp arms.

Accordingly, the exit-passages are not provided in the coupling head, but in the tail ends of the clamp arms. Specifically, the exit-passages are designed such that they are small enough, so that the pivot pin cannot fall out of the clamp arms unintentionally, but can be intentionally pulled out of the through-holes through the exit-passages by exerting a sufficiently high tensile force to the control wire. In this case, the tail end sections of the clamp arms are spread apart and thus deformed, without breaking. For example, the exit-passages may be formed by slits in the tail end sections of the clamp arms. The tail end sections of the clamp arms may be elastically or plastically de-formed, when they are spread apart. In any way, the tail end sections of the clamp arms do not break in order to avoid that parts remain freely in the body of a patient.

Optionally, the coupling head has a U-shaped or bifurcated holding structure which is open on its distal end, wherein the pivot pin is held between the U-legs and extends through sections of the through-hole provided in the U-legs. The proximal ends of the clamp arms are arranged between the U-legs of the coupling head.

An optional embodiment of the present disclosure is characterized in that the clamp housing is directly connected to the sheath device by at least one connecting element, in that each connecting element is fixedly attached to the clamp housing or part of the clamp housing and releasably connected to the sheath device, and in that a release arrangement cooperating with each connecting element is provided and can be actuated by moving the control wire in the proximal direction when the clamp arms have been closed and in particular the control wire has been uncoupled from the clamp device, to release each connecting element and thus, the clamp housing from the sheath device.

In this embodiment of the present disclosure, the clamp housing and the sheath device are directly connected to each other by corresponding connecting elements, which are fixedly provided on the clamp housing or part of the clamp housing and releasably connected to the sheath device. In this way, a very reliable and stable connection between the clamp housing and the sheath device is obtained. Also, the medical device is simple in design and easy to manufacture.

The connecting elements can be actuated in order to release the clamp housing from the sheath device, when the clamp arms have been closed. Specifically, the arrangement is such that when the clamp arms have been closed and the control wire is moved further in the proximal direction the clamp housing is released from the sheath device.

According to a further embodiment of the present disclosure, the sheath device includes a sheath, optionally an extendable coiled sheath, and a connect tube provided on the distal end of the sheath. Optionally, the connect tube is connected to the sheath in such a way, that the connect tube can be rotated relative to the sheath around its central longitudinal axis. For this purpose, a ring groove may be provided in an outer circumferential surface of the connect tube. Engagement members are then fixedly provided on and optionally welded to the sheath, which engage into the ring groove in order to connect/couple the connect tube to the sheath. In this coherence, the engagement members may include a ring shoulder engaging into the ring groove.

Optionally, at least two connecting elements are provided and located with a regular angular offset along the outer circumference of the clamp housing, wherein, optionally, exactly two connecting elements are provided and located on opposite sides of the clamp housing.

A further embodiment of the present disclosure provides, that the connecting elements are provided in the form of resilient, elastically deformable connecting arms, wherein the distal ends of the connecting elements are fixedly attached to the clamp housing and the free proximal ends of the connecting elements form engagement portions that engage corresponding engagement means of the sheath device in order to connect the clamp housing to the sheath device, and that the release arrangement includes a protrusion, that is arranged between and cooperates with the connecting elements in such a way, that the protrusion presses against the connecting elements, elastically deforming them outwardly, so that the engagement portions of the connecting elements are urged outwardly into engagement with the corresponding engagement means of the sheath device, in order to connect the clamp housing to the sheath device, wherein the protrusion is coupled with and in particular fixedly provided on the control wire in such a way, that if after closing the clamp arms the control wire is moved further in the proximal direction the protrusion is moved together with the control wire out of engagement from the connecting elements with the result that the latter are deformed inwardly by their elastic restoring force and the engagement portions of the connecting elements come out of engagement of the corresponding engagement means of the sheath device to release the clamp housing from the sheath device.

According to an optional embodiment, the protrusion is formed by the coupling head. In other words, the coupling head may form a protrusion which presses against the connecting elements deforming them outwardly.

Optionally, the connecting elements may be welded to the clamp housing, in particular by means of a spot welding.

An optional development of this embodiment provides, that the connecting elements are provided with bulged sections, which are in particular provided at the free end of the connecting elements, and that the protrusion is arranged between and cooperated with the bulged sections of the connecting elements to deform the connecting elements outwardly, wherein the connecting elements are deformed inwardly by their elastic restoring force when the protrusion is moved out of engagement from the bulged sections.

In this embodiment, the engagement portions of the elastic connecting elements are actively held in engagement with the engagement means provided in the clamp base by the engagement of the protrusion and the connecting elements, in particular the inwardly bulged sections of the connecting elements. Once this engagement is no more existent, because the control wire is pulled back in the proximal direction so far, that the protrusion is no more arranged/located between the connecting elements/the bulged sections, the connecting elements are elastically deformed inwardly by their restoring force. In other words, the connection between the sheath device and the clamp base is passively released by moving the protrusion of the control wire out of the range of the connecting elements or bulged sections thereof.

A further embodiment of the present disclosure provides that the clamp housing is connected to the sheath device by a push-in connection thus forming an overlapping section, wherein, optionally, the proximal end of the clamp housing is inserted into the distal end of the sheath device, and that the engagement means are provided as recesses or through-holes in the inner circumferential wall of the sheath device, wherein, optionally, the engagement portions of the connecting elements are formed as outwardly directed engagement fingers.

Optionally, the engagement means of the sheath device and corresponding apertures are provided in the overlapping section of the sheath device and the clamp housing such that the engagement portions of the connecting elements are pressed outwardly through the apertures in the clamp housing into the engagement means of the sheath device in order to connect the clamp housing to the sheath device.

The connecting elements may have a straight section, which is slanted inwardly with regard to a central longitudinal axis of the clamp housing if viewed in the proximal direction, wherein the slanting angle is in particular 3° to 15° and optionally 5°.

According to an embodiment of the present disclosure, the connecting elements are fixedly connected to the clamp housing at the distal end section thereof, wherein, in particular, the distal ends of the connecting elements are directed radially outwardly and extend out into corresponding holding apertures provided in the clamp housing and are optionally fixed therein by welding.

Optionally, the clamp housing includes two bearing arms extending in the distal direction from a clamp base and the connecting elements are fixedly attached to the bearing arms at the free end sections thereof, wherein, in particular, a guide pin is held between the two bearing arms and the connecting elements are provided on the distal side of the guide pin.

In a further elaboration of the medical device according to the present disclosure, at least one clamp arm, in particular both clamp arms may include at their proximal ends tail end sections on opposite lateral sides, which are able to engage behind at least one shoulder of the clamp housing in order to lock the clamp arms to the clamp housing additionally to the holding noses or holding humps formed in the guide grooves which capture the guide pin in the distal ends of the guide grooves. Optionally, the tail end sections of the clamp arms form hooks that engage behind the at least one shoulder of the clamp base in order to lock the clamp arms to the clamp base. In concrete terms, the tail end sections of both clamp arms may form two opposing hooks. It is also conceivable, that only one tail end section of each clamp arm forms a hook. Furthermore, it is also possible that only one tail end section of one clamp arm forms a hook, wherein the other clamp arm does not include a hook.

The shoulder can be formed by an annular projection of the clamp base, wherein the annular projection in particular forms the distal end face of the clamp housing, in particular of the clamp base with a central opening, through which the tail ends of the clamp arms extend into the clamp base when the clamp arms are fully closed.

It is also conceivable that the proximal ends of the clamp arms are designed such that they do not engage behind at least one shoulder of the clamp housing. In this case, locking of the closed clamp arms is realized otherwise, for example only by the guide pin being captured by the holding noses or holding humps formed in the guide grooves.

BRIEF DESCRIPTION OF DRAWINGS

Embodiments of the present disclosure will in the following be described making reference to the attached drawings. In these drawings

REFERENCE SIGNS

Figure 1:
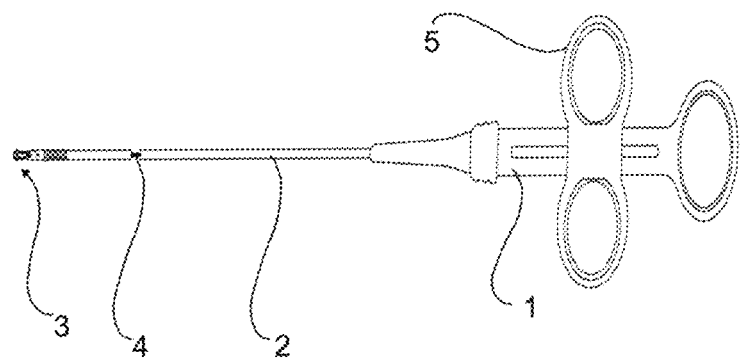
FIG. 1 shows a front view of a medical device according to a first embodiment of the present disclosure.
Figure 2:
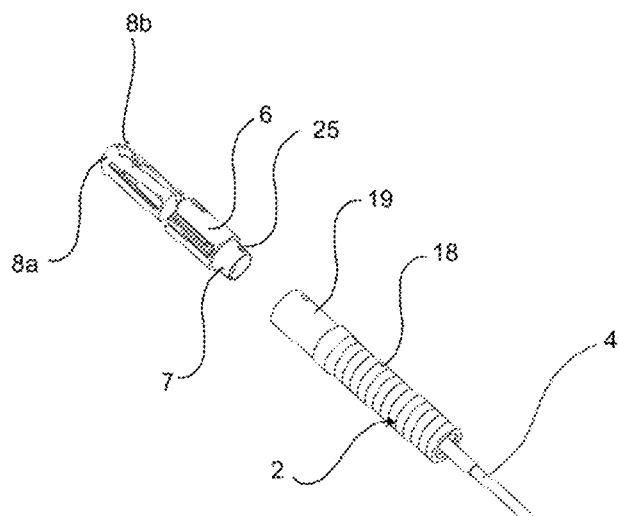
FIG. 2 shows in enlarged scale the front, distal part of the medical device of FIG. 1 in partially sectioned view, with a clamp device separated from a sheath device.
Figure 3:
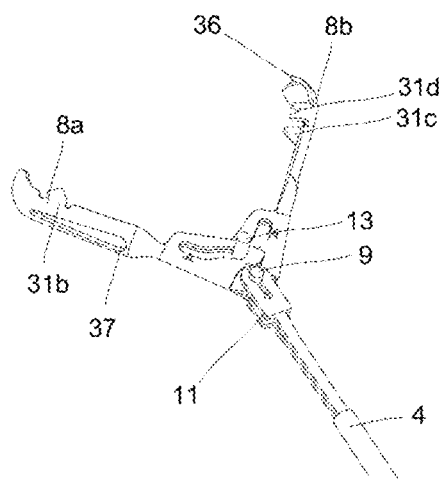
FIG. 3 is a perspective view of the clamp device with the clamp arms in fully open state.
Figure 4:
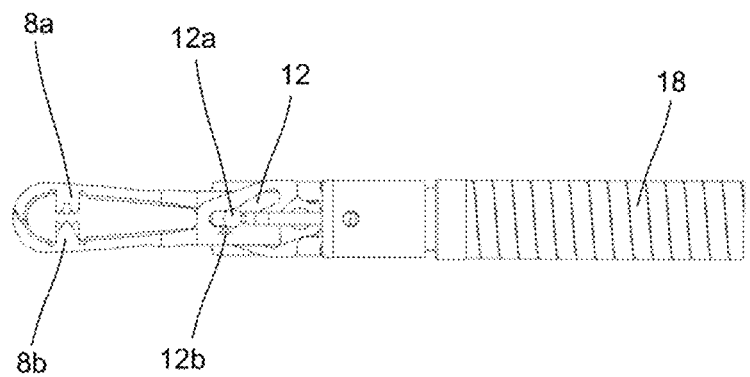
FIG. 4 is a partially sectioned view of the clamp device with closed clamp arms, FIG. 5 corresponds to FIG. 4 and shows the clamp device with the clamp arms in fully closed and secured position, FIG. 6 corresponds to FIG. 5 and shows the process of uncoupling a control wire from the clamp arms.
Figure 5:
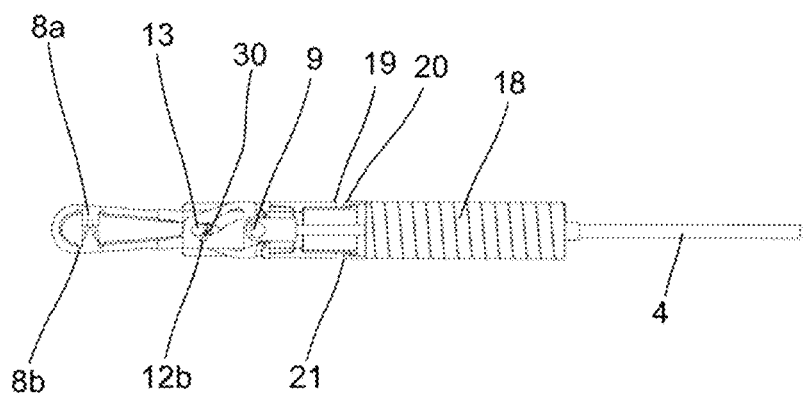
Figure 6:
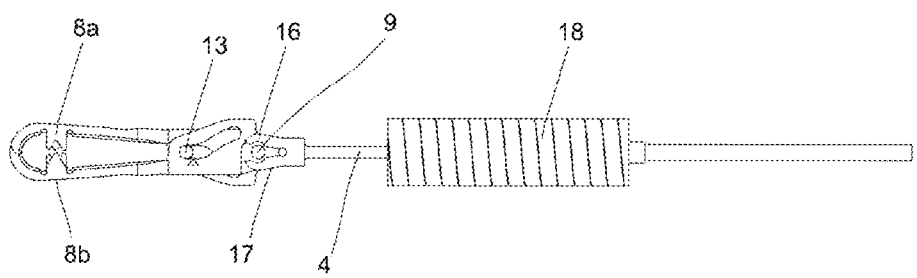

1—handle; 2—sheath device; 3—clamp device; 4—control wire; 5—actuator; 6—clamp housing; 7—clamp base; 8a, 8b—clamp arm; 9—pivot pin; 10—through-hole; 11—coupling head; 12—guide groove; 12a—straight distal end section; 12b—recess; 13—guide pin; 14a, 14b—bearing arm; 15—exit-passage; 16—distal end portion; 17—distal end portion; 18—sheath; 19—connect tube; 20—ring groove; 21—engagement member; 22—connecting element; 23—engagement portion; 24—engagement means; 25—aperture; 26—holding aperture; 27—straight section; 28—bulged section; 29—protrusion; 30—holding nose; 31a, 31b, 31c, 31d—barb; 32—grasping section; 33—V-shaped protrusion; 34—V-shaped recess; 35—notch; 36—engagement contour; 37—through-opening; 38—through-hole; 39—exit-passage; 40—guide pin; 41—inner opening; 42—middle section; 43—through-slit; 44—holding hump; 45—through-slit.

DETAILED DESCRIPTION OF EMBODIMENTS

In FIG. 1 to FIG. 15, a first embodiment of a medical device according to the present disclosure is shown. The medical device is used to set clamps for causing hemostasis of blood vessels located along the gastrointestinal tract, wherein the clamps are delivered to a target site through an endoscope.

The medical device includes a handle 1, a sheath device 2, which is attached to the handle 1, and a clamp device 3 which is provided on a distal end of the sheath device 2. A control wire 4 extends through the sheath device 2 and is at its proximal end connected to an actuator 5, which is slidingly held on the handle 1 and can be actuated to reversibly move the control wire 4 in the distal and proximal directions.

The clamp device 3 includes a clamp housing 6 with a clamp base 7 formed as a sleeve and two clamp arms 8a, 8b, which are each coupled to the distal end of the control wire 4. Optionally, the two clamp arms 8a, 8b are separate elements/components that are coupled to the control wire 4 by means of a pivot pin 9, which is provided at a distal end section of the control wire 4 and extends through corresponding through-holes 10 provided in a coupling head 11 formed at the distal end section of the control wire 4.

The coupling head 11 has a U-shaped or bifurcated holding structure which is open on its distal end, and the clamp arms 8a, 8b are partly arranged between the U-legs of the U-shaped holding structure. The pivot pin 9 is held between the U-legs and extends through the through-holes 10 of the coupling head 11, which in turn extend laterally outwards of or laterally protrudes from the open lateral side of the U-shaped holding structure.

The two clamp arms 8a, 8b are coupled to the distal end of the control wire 4 so that they can be rotated around a common pivot axis formed by the pivot pin 9 in order to open and close them. Each clamp arm 8a, 8b is provided with a guide groove 12, and the guide grooves 12 of the clamp arms 8a, 8b partially overlap each other.

The clamp device 3 further includes a guide pin 13, which is attached to the clamp housing 6 and extends through the guide grooves 12 in the overlap-ping parts thereof, so that by the engagement of the guide pin 13 and the guide grooves 12 a movement of the control wire 4 in the proximal direction is translated into a closing movement of the clamp arms 8a, 8b, and a movement of the control wire 4 in a distal direction is translated into an opening movement of the clamp arms 8a, 8b around the pivot axis. In the present embodiment the guide pin 13 is held between two bearing arms 14a, 14b of the clamp housing 6 extending upright from the distal end of the clamp base 7 forming a bifurcated structure, the clamp arms 8a, 8b being arranged between those bearing arms 14a, 14b extending laterally outward of the structure.

Figure 7:
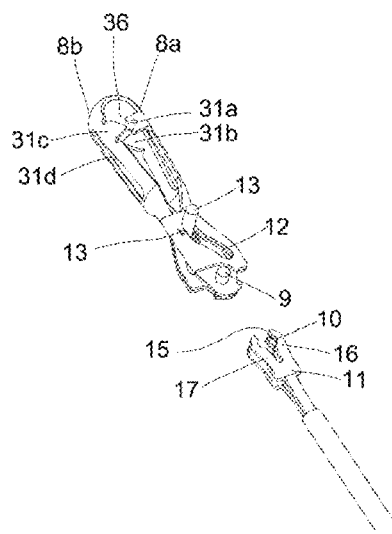
FIG. 7 is a perspective view of the distal part of the medical device and shows the clamp device uncoupled from the control wire.
Figure 8:
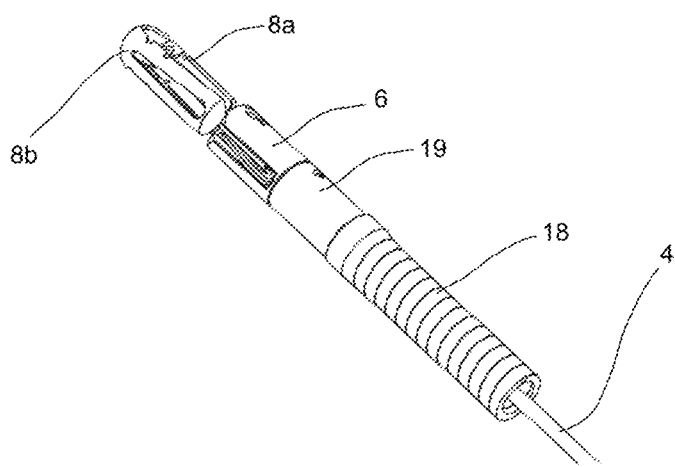
FIG. 8 is a perspective view of the distal part of the medical device with the clamp arms in fully closed position.
Figure 9:
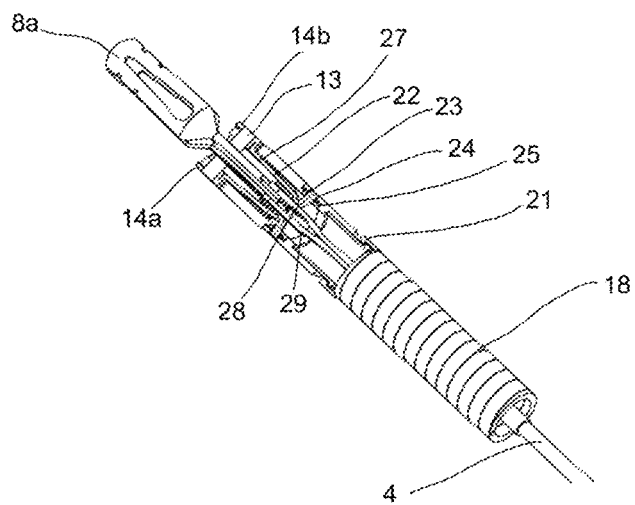
FIG. 9 to FIG. 10 are partially sectioned views of the distal part of the medical device showing the release of the clamp housing from the sheath device.
Figure 10:
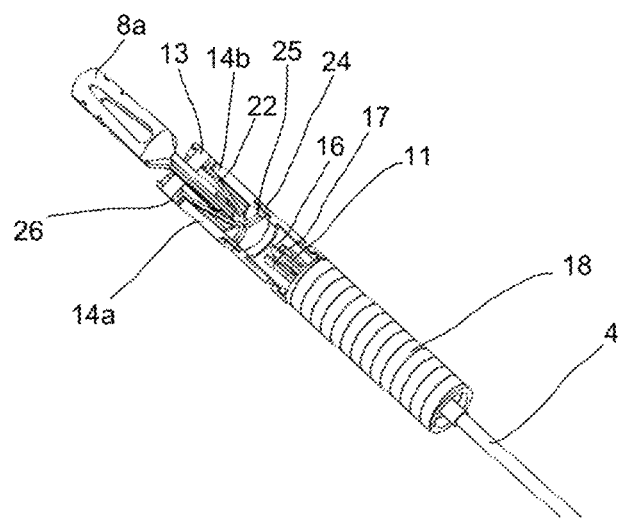
Figure 11:
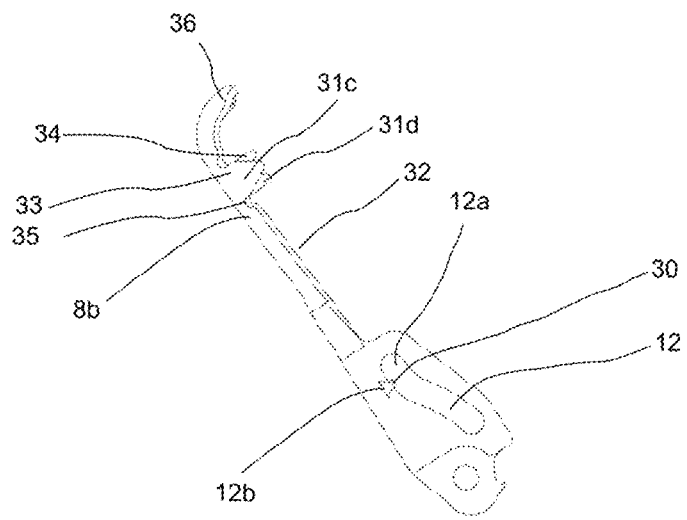
FIG. 11 is a front view of a clamp arm of the clamp device.
Figure 12:
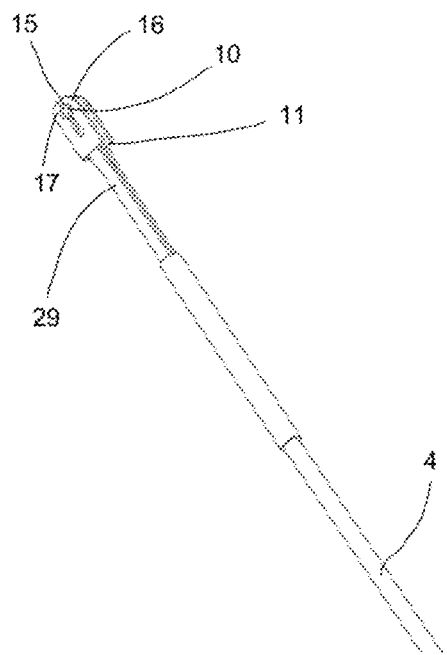
FIG. 12 is a perspective view of the control wire with a protrusion and a coupling head.
Figure 13:
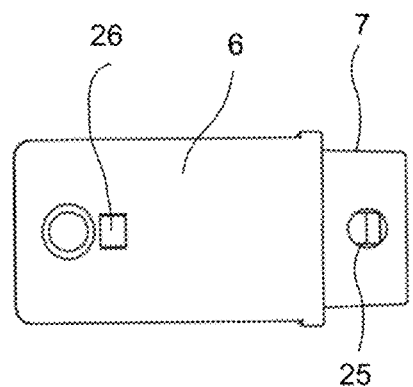
FIG. 13 is a perspective view of the clamp housing.
Figure 14:
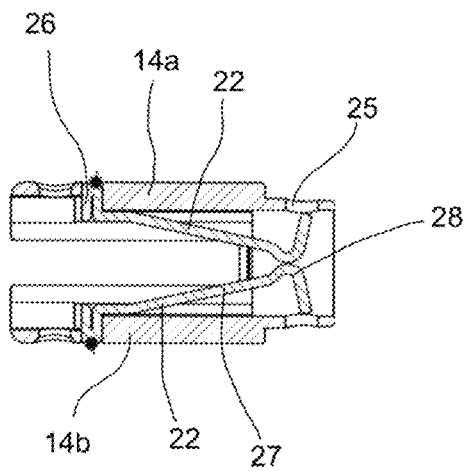
FIG. 14 is a sectioned view of the clamp housing.
Figure 15:
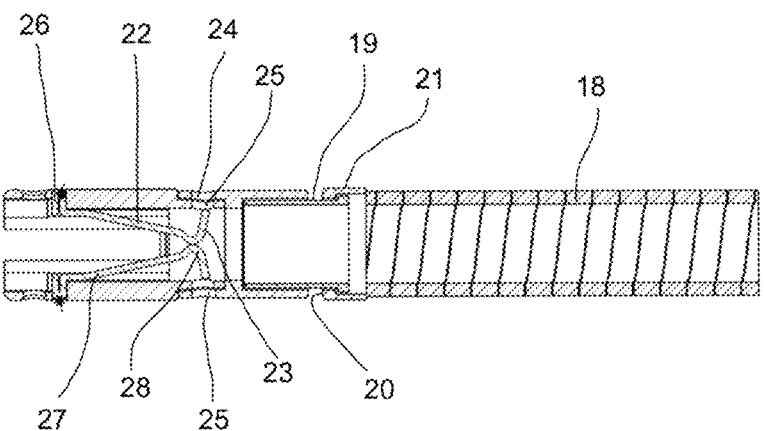
FIG. 15 is a sectioned view of the clamp housing attached to the sheath device.

As shown in FIG. 7 the through-holes 10 for the pivot pin 9 in the coupling head 11 are open to their distal side. In other words, exit-passages 15 are provided in the distal end of the coupling head 11 at the distal sides of the through-holes 10, through which after closing the clamp arms 8a, 8b the pivot pin 9 can be pulled out of the through-holes 10 spreading apart the distal end portions 16, 17 of the coupling head 11 on the opposite sides of the exit-passage without breaking them. In this way, the control wire 4 is uncoupled from the clamp arms 8a, 8b and, accordingly, the clamp device 3. The exit-passages 15 are here formed by slits in the distal end of the clamp arms 8a, 8b.

As it can be seen in FIG. 7, the distal end portions 16, 17 of the coupling head 11 are plastically deformed, when they are spread apart.

The sheath device 2 includes a coiled sheath 18, which is connected to the handle 1, and a connect tube 19, which is provided on a distal end of the coiled sheath 18, so that the sheath device 2 forms an inseparable unit. The connect tube 19 is connected to the sheath 18 in such a way, that the connect tube 19 can be freely rotated relative to the sheath 18 around its central longitudinal axis. For this purpose, a ring groove 20 is provided in an outer circumferential surface of the connect tube 19 and engagement members 21 are fixedly provided on and optionally welded to the sheath 18, which engage into the ring groove 20 in order to connect the tube 19 rotatable to the sheath 18. In the present embodiment the engagement members 21 are formed as engagement fingers provided on a holding sleeve, which is welded to the sheath 18.

The sheath device 2 is connected to the clamp housing 6 by means of two connecting elements 22 in the form of elastic connecting arms that are positioned on opposite sides of the clamp housing 6. Optionally, the distal ends of the connecting elements 22 are fixedly attached to the clamp housing 6, whereas the free proximal ends of the connecting elements 22 form engagement portions 23 that engage corresponding engagement means 24 provided in the inner circumferential surface of the connect tube 19, in order to couple the clamp housing 6 to the sheath device 2. Here, the clamp housing 6 is connected to the sheath device 2 by a push-in connection, wherein the proximal end of the clamp housing 6 is inserted/extends into the distal end of the connect tube 19 of the sheath device 2. In the overlapping sections of the connect tube 19 the engagement portions 23 of the sheath device 2 are provided in the form the through holes, and apertures 25 corresponding to the through holes are provided in the clamp housing 6 such that the engagement portions 23 of the connecting elements 22 are pressed outwardly through the apertures 25 and the clamp housing 6 into the engagement means 24 of the sheath device 2 in order to connect the clamp housing 6 to the sheath device 2.

The connecting elements 22 have inwardly bulged sections. Further, the distal ends of the connecting elements 22 are directed radially outwardly and extend into corresponding holding apertures 26 provided in the clamp housing 6, and are optionally fixed therein by welding, presently by a spot welding. The connecting elements 22 further have a straight section 27 following the distal end of the connecting elements 22, which is slanted inwardly with regard to the central longitudinal axis of the clamp housing if used in the proximal direction, wherein the slanting angle is 5°. Between the straight section 27 and the engagement portions 23 of the connecting elements 22 an inwardly bulged section 28 is provided at the proximal end of the connecting elements 22.

A release arrangement for disconnecting the clamp housing 6 from the connect tube 19 is provided. This release arrangement includes a protrusion 29 provided on the control wire 4. The protrusion 29 cooperates with and is located between the inwardly bulged sections 28 of the connecting elements 22 to press the inwardly bulged sections 28 outwardly elastically deforming the connecting elements 22 in such a way that their free ends are pressed. When the control wire 4 is pulled proximally and the protrusion 29 comes out of engagement of the connecting elements 22, the bulged sections 28 are re-deformed inwardly by their elastic restoring force to obtain their original shape and the engagement portions 23 come out of engagement of the engagement means 24 of the connect tube 19.

In use, the clamp device 3 is delivered to the target site through an endoscope, and the clamp device 3 is fixed at a predetermined position on the target site to a blood vessel. In order to pinch the blood vessel the clamp arms 8a, 8b can be repeatedly opened and closed by moving the control wire 4 in the distal and proximal direction by means of the actuator 5.

Once the clamp device 3 has been set, the clamp arms 8a, 8b are to be disconnected from the control wire 4. For this purpose, the control wire 4 is pulled in proximal direction in order to fully close the clamp arms 8a, 8b and secure them in the closed position, as depicted in FIG. 7. This figure shows, that the guide grooves 12 have a straight, axially extending distal end section 12a, in which the guide pins 13 can move without incurring further rotation of the clamp arms 8a, 8b. When the guide pin 13 reaches the distal end positions in the guide grooves 12, it is secured/locked in this position by holding noses 30 provided on the clamp arms 8a, 8b. The holding noses 30 extend into the straight end sections 12a of the guide grooves 12 from a lateral side thereof and are designed in such a way, that they allow the guide pin 13 to pass them to reach the proximal ends of the guide grooves 12 but prevent passing of the guide pin 13 in the opposite direction. Optionally, the holding noses 30 are designed such that they elastically deform into recesses 12b formed as through-openings. The recesses 12b are formed in the clamp arms 8a, 8b laterally to the guide grooves 12 in proximity to the holding noses 30, such that the holding noses 30 can deform elastically to allow the guide pin 13 to pass the holding noses 30 and to reach its distal end position in the guide grooves 12. After that the guide pin 13 has passed the holding noses 30, the holding noses 30 regain their initial form by their elastic restoring force to engage behind the guide pin 13, when the guide pin 13 has reached its final position. The holding noses 30 are designed such that they cannot be deformed to reopen the guide grooves 12 when the guide pin 13 presses against their distal sides, so that the guide pins 13 are captured in their distal end positions in the guide grooves 12. In this way, the clamp arms 8a, 8b are securely locked to the clamp base 7 and accordingly to the clamp housing 6.

In order to improve the grasping of tissue positioned between the clamp arms 8a, 8b and to minimize the risk of loosening the clamp device 3 when fixed to tissue inside the body of a patient, each clamp arm 8a, 8b includes two barbs 31a, 31b, 31c, 31d arranged on laterally opposite sides of the clamp arm 8a, 8b in a grasping section 32. The barbs 31a, 31b, 31c, 31d are formed such that each barb points in the direction of a corresponding, opposite barb of the other clamp arm 8a, 8b. For example, on FIG. 11 it is visible that the clamp arm 8b includes two barbs 31c, 31d pointing towards the other clamp arm 8a. The barb 31c includes a clamping contour in the form of a V-shaped protrusion 33, wherein the barb 31d includes a clamping contour in the form of a V-shaped recess 34 which is complementary to the V-shaped protrusion 33. On FIG. 7, it is visible that the barb 31a of the clamp arm 8a has a V-shaped recess 34 and the barb 31b has a V-shaped protrusion, each complementary to the corresponding barbs 31c, 31d of the other clamp arm 8b, respectively. To avoid unintended damages of blood vessels clamped between the clamp arms 8a, 8b, the corners of the V-shaped protrusions 33 and the corners of the V-shaped recesses 34 are round chamfers. Furthermore, rounded notches 35 are provided adjacent to the barbs 31a, 31b, 31c, 31d.

The distal end of the grasping section 32 of each clamp arm 8a, 8b is bent inwards towards the other clamp arms 8a, 8b. An engagement contour 36, in the present case a zigzag profile, is formed at the distal end of each clamp arm 8a, 8b. The engagement contours 36 of the clamp arms 8a, 8b are complementary to each other so that they engage with each other when the clamp arms 8a, 8b are closed. In order to allow grasped tissue to expand, the clamp arm 8a, 8b includes a through-opening 37 formed in the grasping section 32 extending in the longitudinal direction of the clamp arm 8a, 8b.

If the control wire 4 is further pulled back, further movement of the clamp arms 8a, 8b is no more possible, and insofar the pivot pin 9 is pulled out of the through-holes 10 of the coupling head 11 through the exit-passages 15 on the distal side of the coupling head 11. During this process, the distal end portions 16, 17 of the coupling heads 11 located on the opposite sides of the exit-passages 15 are plastically spread apart to open the exit-passages 15.

In order to uncouple/release the clamp housing 6 from the sheath device 2, the control wire 4 is further pulled back in proximal direction, so that the protrusion 29 of the coupling head 11 comes out of engagement from the inwardly bulged sections 28 of the connecting elements 22 so that the connecting elements 22 regain the initial shape in which their free ends come out of engagement from the engagement means 24 of the connect tube 19 of the sheath device 2.

FIG. 16 to FIG. 27 show a further embodiment of the medical device according to the present disclosure.

This medical device is very similar to the one disclosed in FIG. 1 to FIG. 15 and includes similarly a handle (not shown), a sheath device 2 being attached to the handle and a clamp device 3 provided on the distal end of the sheath device 2. A control wire 4 extends through the sheath device 2 and is at its proximal end connected to an actuator (not shown) which is slidingly held on the handle and can be actuated to reversibly move the control wire 4 in the distal and proximal directions.

The clamp device 3 includes a clamp housing 6 with a clamp base 7 formed as a sleeve and two clamp arms 8a, 8b, which are each coupled to the distal end of the control wire 4. Optionally, the two clamp arms 8a, 8b are separate elements/components that are coupled to the control wire 4 by means of a pivot pin 9, which is provided at a distal end section of the control wire 4 and extends through corresponding through-holes 10 provided in a coupling head 11 formed at the distal end section of the control wire 4.

Figure 18:
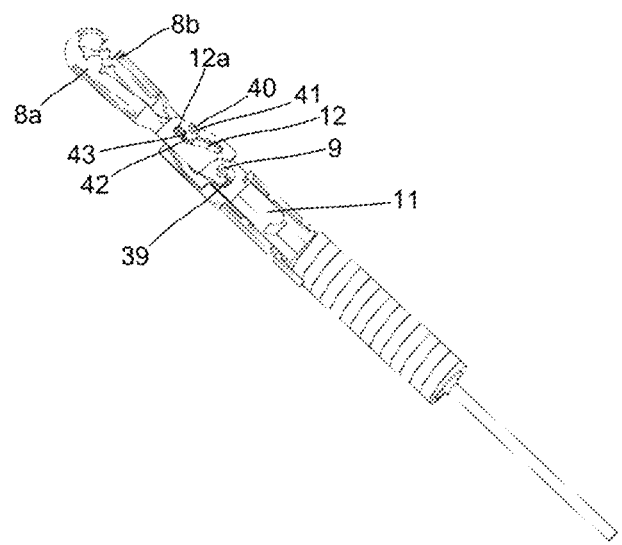
FIG. 18 is a partially sectioned view of the medial device with closed clamp arms, FIG. 19 corresponds to FIG. 18 and shows the clamp device with the clamp arms in fully closed and secured position.
Figure 19:
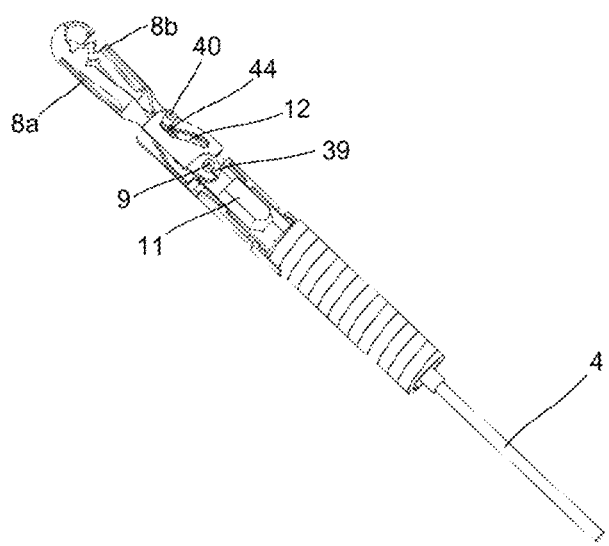
Figure 20:
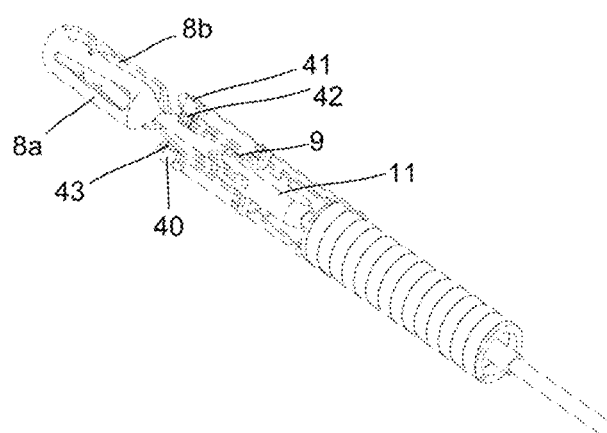
FIG. 20 is another partially sectioned perspective view with the clamp arms in fully closed and secured position.
Figure 21:
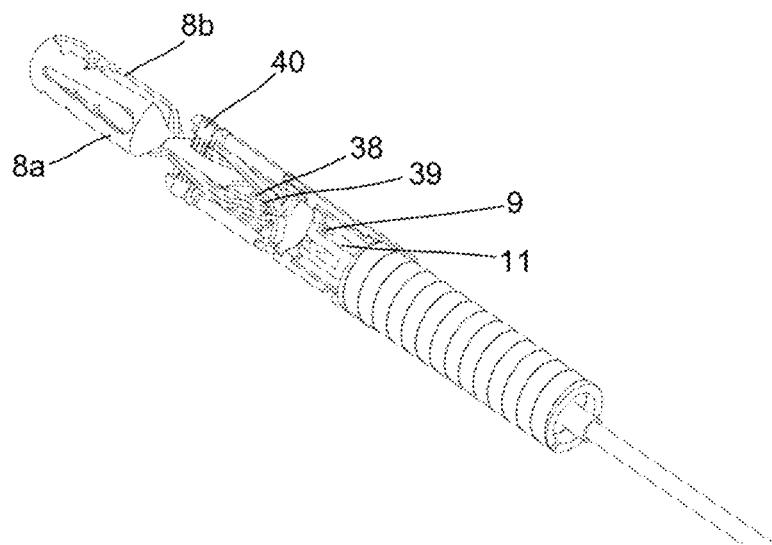
FIG. 21 is a partially sectioned perspective view of the distal part of the medical device and shows the clamp device uncoupled from the control wire.
Figure 22:
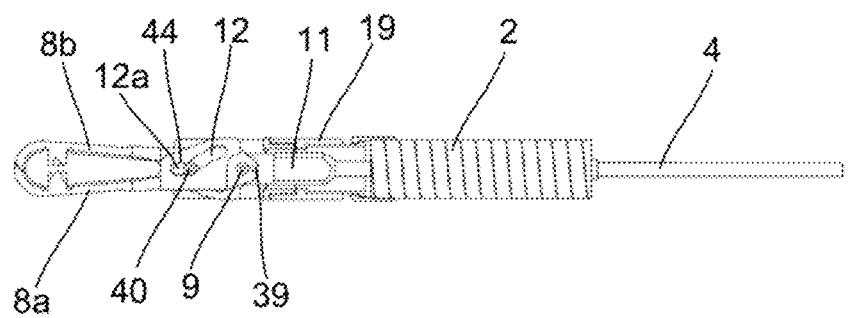
FIG. 22 is a partially sectioned view of the distal part of the medical device showing the clamp arms in fully closed position.
Figure 26:
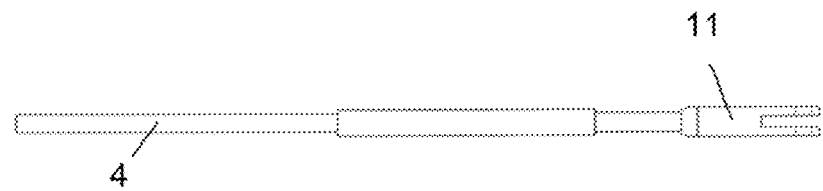
FIG. 26 shows a top view of the distal part of the control wire.
Figure 27:
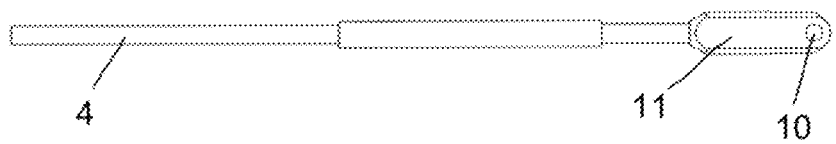
FIG. 27 shows a side view of the distal part of the control wire.
Figure 28:
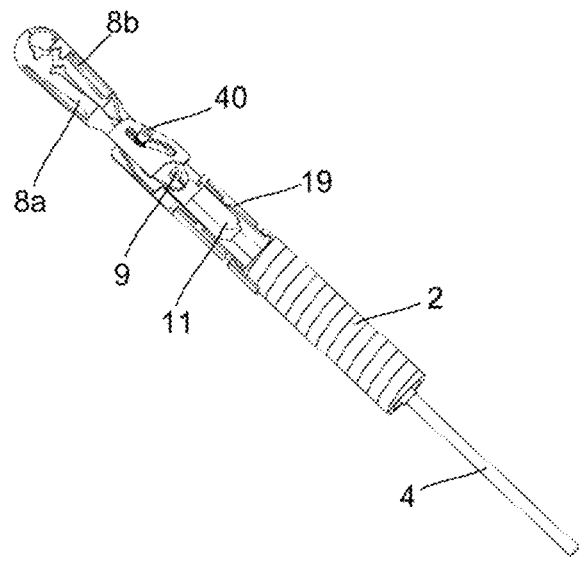
FIG. 28 shows a partially sectioned perspective view of the distal part of a medical device according to a further embodiment of the present disclosure.
Figure 29:
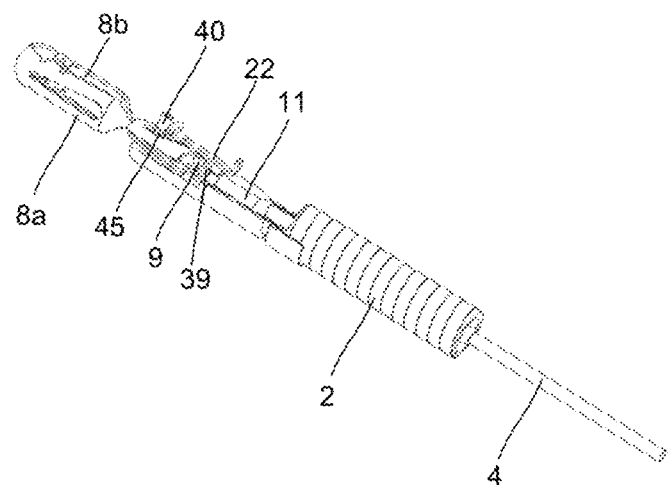
FIG. 29 shows a partially sectioned perspective view of the medical device of FIG. 30 with closed clamp arms.
Figure 30:
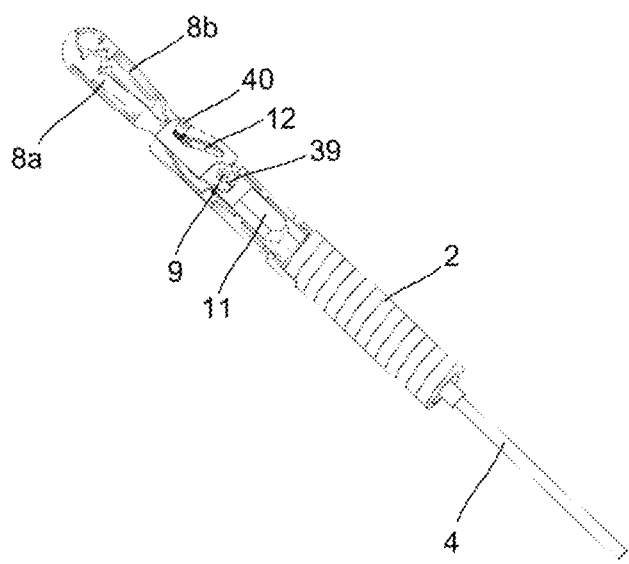
FIG. 30 is a partially sectioned perspective view of the distal part of the medical device of FIG. 28 with the clamp arms in fully closed and secured position.
Figure 31:
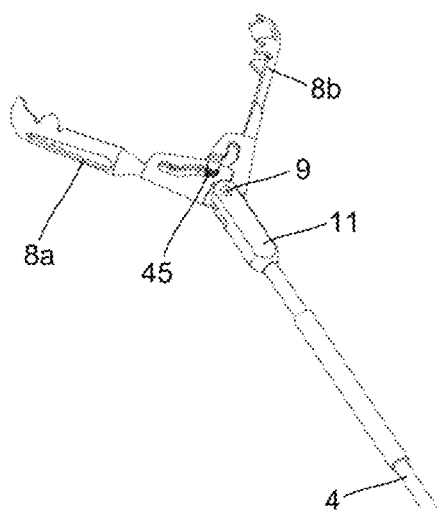
FIG. 31 is a partially perspective view of the clamp arms in fully opened position and the distal end of the control wire.

As it is visible in FIG. 26 and FIG. 27, the coupling head 11 has a U-shaped holding structure which is open on its distal end, and the clamp arms, as it is visible for example on FIG. 18 and FIG. 20, are partly arranged between the U-legs of the U-shaped holding structure. The pivot pin 9 is held between the U-legs and extends through the through-holes 10 of the coupling head 11.

The two clamp arms 8a and 8b are coupled to the distal end of the control wire 4 so that they can be rotated around a common pivot axis formed by the pivot pin 9 in order to open and close them. Each clamp arm 8a, 8b is provided with a guide groove 12, the guide grooves 12 of the clamp arms 8a, 8b partially overlapping each other.

Figure 23:
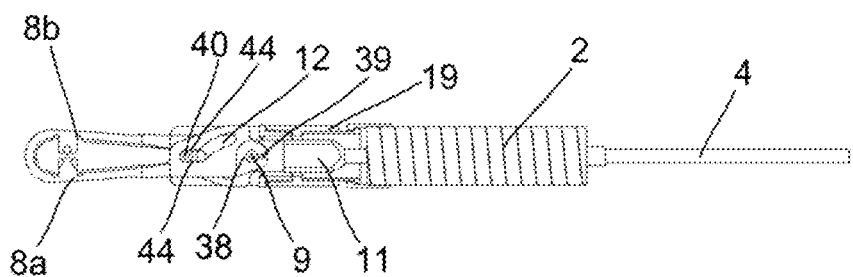
FIG. 23 is a partially sectioned view of the distal part of the medical device with the clamp arms in fully closed and secured position.
Figure 24:
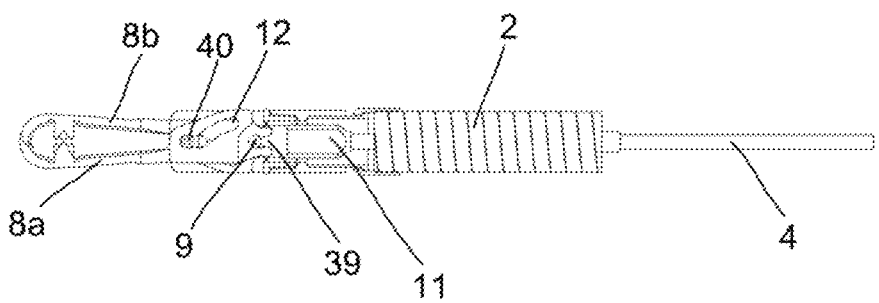
FIG. 24 is a partially sectioned view of the distal part of the medical device showing the process of uncoupling the control wire from the clamp arms.

The pivot pin 9 extends through corresponding through-holes 38 provided in the proximal end sections of the clamp arms 8a, 8b. Exit-passages 39 are provided in the tail ends of the clamp arms 8a, 8b. After closing the clamp arms 8a, 8b, the pivot pin 9 can be pulled out of engagement from the trough-holes 38 and from the clamp arms 8a, 8b, thereby spreading apart the tail end sections of the clamp arms 8a, 8b as shown in FIG. 23 and FIG. 24. Spreading apart the tail end sections of the clamp arms 8a, 8b without breaking them is realized by proximal movement of the control wire 4 in order to uncouple the control wire 4 from the clamp arms 8a, 8b.

The clamp device 3 further includes a guide pin 40, which is attached to the clamp housing 6 and extends through the guide grooves 12 in the overlap-ping parts thereof. Thus, by the engagement of the guide pin 40 and the guide grooves 12 a movement of the control wire 4 in the proximal direction is translated into a closing movement of the clamp arms 8a, 8b. A movement of the control wire 4 in the distal direction is translated into an opening movement of the clamp arms 8a, 8b around the pivot axis. In the present embodiment, the guide pin 40 is held between two bearing arms 14a, 14b of the clamp housing 6 extending upright from the distal end of the clamp base 7 forming a bifurcated structure, the clamp arms 8a, 8b being arranged between those bearing arms 14a, 14b extending laterally outward of the structure.

The guide pin 40 has a tubular shape over its entire length having an inner opening 41 and includes in its longitudinal direction one middle section extending through the guide grooves 12 of the clamp arms 8a, 8b. As it is visible in FIG. 18, FIG. 19, FIG. 20, and FIG. 21, this middle section 42 is radially deformable. Optionally, a plurality of through-slits 43 extending in the longitudinal direction of the guide pin 40 are spaced apart over the entire circumference of the guide pin 40.

Figure 25:
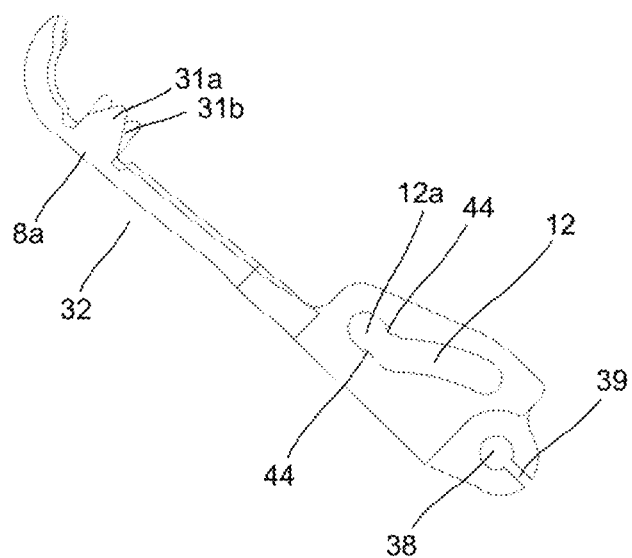
FIG. 25 shows a side view of a clamp arm.

As in particular shown in FIG. 25, the clamp arms 8a, 8b are provided with holding humps 44 extending into the guide grooves 12 from lateral sides thereof. Each clamp arm 8a, 8b is provided with two holding humps 44 extending from opposite lateral sides of the respective guide groove 12. The holding humps 44 have the shape of a segment of a circle.

When the guide pin 40 reaches the distal end position in the guide groove 12 after having passed the holding humps 44 by a radial deformation of the middle section 42 of the guide pin 40, it is secured/locked in this distal end position by the holding humps 44. The holding humps 44 extend into the straight end sections 12a of the guide grooves 12 from both lateral sides thereof. It is not intended that the holding humps 44, contrary to the holding noses 30 of the embodiment shown in FIG. 1 to FIG. 15, deform elastically. Moreover, the middle section 42 of the guide pin 40 is intended to deform elastically when passing the holding humps 44. After that the guide pin 40 has passed the holding humps 44, the guide pin 40 regains its initial form by the elastic restoring force of the middle section engaging behind the holding humps 44 and thus locking the clamp arms 8a, 8b in their closed state. In this way, the clamp arms 8a, 8b are securely locked to the clamp base and accordingly to the clamp housing 6.

Figure 16:
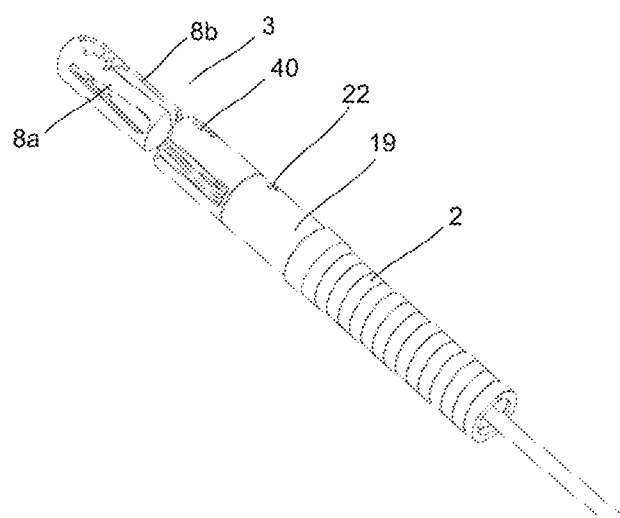
FIG. 16 shows a perspective view of a medical device according to a further embodiment of the present disclosure.
Figure 17:
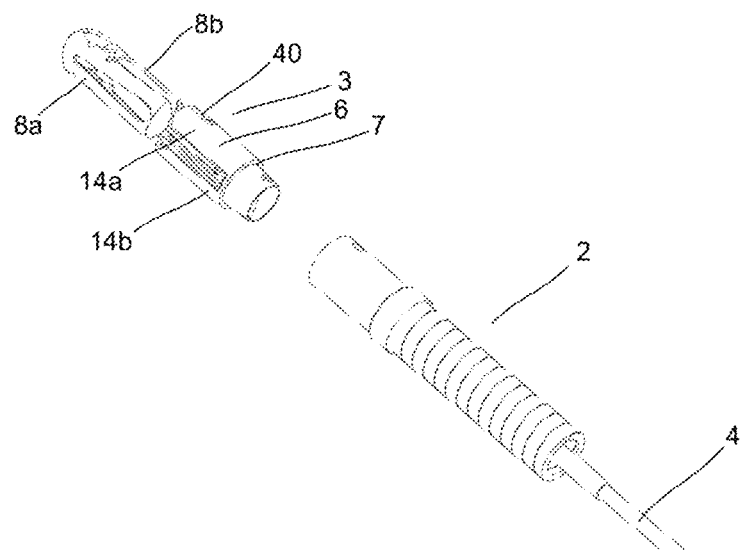
FIG. 17 shows a perspective view of the medical device of FIG. 16 with a clamp device separated from the sheath device.

As it is shown in FIG. 16 and FIG. 17, the sheath device 2 includes a coiled sheath 18 and a connect tube 19 identical to the embodiment shown in FIG. 1 to FIG. 15.

The sheath device 2 is connected to the clamp housing 6 by means of two connecting elements 22 in the form of elastic connecting arms that are positioned on opposite sides of the clamp housing 6. The connection of the sheath device 2 of the clamp housing as well as the release arrangement for disconnecting the clamp housing 6 from the connect tube 19 is identical to the embodiment shown in FIG. 1 to FIG. 15, so that reference is made to the description of this embodiment. The protrusion 29 formed by the coupling head 11 of the control wire 4 cooperates with the connecting element 22 in the same way as described in the embodiment shown in FIG. 1 to FIG. 15.

In order to improve the grasping of tissue positioned between the clamp arms 8a, 8b to minimize the risk of loosening the clamp device 3 when fixed to tissue inside the body of a patient, each clamp arms 8a, 8b includes two barbs 31a, 31b, 31c, 31d arranged on laterally opposite sides of the clamp arms 8a, 8b in a grasping section 32. The grasping section 32 of the clamp arms 8a, 8b is identical to the embodiment shown in FIG. 1 to FIG. 15. Reference is made in this coherence to this embodiment.

In FIG. 28 to FIG. 31, a further embodiment of a medical device according to the present disclosure is shown. This medical device differs from the embodiment shown in FIG. 16 to FIG. 27 only in that the guide pin 40 does not include a plurality of through-slits 43 extending in the longitudinal direction of the guide pin 40, but a through-slit 45 which is formed helically over the middle section 42 of the guide pin 40. In other words, the middle section 42 of the guide pin 40 is formed like a spiral spring which allows to be easily deformed and in particular squeezed radially when the guide pin 40 has to pass the holding humps 44 extending into the guide grooves 12.

INDUSTRIAL APPLICABILITY

The present disclosure provides a clamp device for tissue hemostasis or closure and a medical device for tissue hemostasis or closure that are easy to operate as well as easy to manufacture and assemble, and that can operate in a reliable manner. By providing the holding noses on the clamp arms of the clamp device, the guide pin is captured in the distal ends of the guide grooves by means of the holding noses, thus locking the clamp arms to the clamp housing, when the clamp arms are fully closed and should remain in the patient's body. The holding noses deform elastically, when the guide pin passes them. In this way, further locking elements are no more necessary and a very reliable and stable locking of the clamp arms is obtained.

What is claimed is:

1. A clamp device for tissue hemostasis or closure, comprising a clamp housing, with a clamp base in a form of a sleeve, and
   at least two clamp arms,
      wherein the clamp arms are able to be coupled to a distal end of a control wire of a medical device, and wherein the clamp device is actuable to open and close the clamp arms,
   wherein the clamp device comprises
   exactly two clamp arms, which are provided as separate elements, wherein the clamp arms are coupled or are able to be coupled at their proximal ends to each other, such that the clamp arms are able to be rotated around a common pivot axis, wherein each of the clamp arms is provided with a guide groove and guide grooves of the clamp arms partially overlap each other, and
   a guide pin, which is attached to the clamp housing and extends through the guide grooves in overlapping parts of the guide grooves, so that by an engagement of the guide pin and the guide grooves a movement of the pivot axis is translated into a closing movement of the clamp arms or into an opening movement of the clamp arms around the pivot axis,
      wherein holding noses are provided on the clamp arms, with the holding noses extending into the guide grooves from a lateral side thereof and being designed in such a way that they allow the guide pin to pass them to reach distal ends of the guide grooves but prevent passing of the guide pin in an opposite direction.

2. The clamp device according to claim 1, wherein each of the clamp arms comprises exactly one holding nose extending into a respective guide groove.

3. The clamp device according to claim 1, wherein the guide grooves have a straight, axially extending distal end section, in which the guide pin is able to move without incurring rotation of the clamp arms and the holding noses extend into the straight distal end sections, and/or recesses, formed as through-openings, are formed in the clamp arms laterally to the guide grooves in proximity to the holding noses such that the holding noses are able to deform elastically, to allow the guide pin to pass the holding noses and reach its distal end position in the guide grooves.

4. The clamp device according to claim 1, wherein the guide pin is held between two bearing arms of the clamp housing extending in a distal direction from the clamp base, at free end sections of the bearing arms.

5. The clamp device according to claim 1, wherein the clamp arms are coupled at their proximal ends to a pivot pin defining the common pivot axis.

6. A clamp device for tissue hemostasis or closure, comprising a clamp housing, with a clamp base, which is in a form of a sleeve, and
   at least two clamp arms,
      wherein the clamp arms are able to be coupled to a distal end of a control wire of a medical device, and wherein the clamp device is actuable to open and close the clamp arms,
   wherein the clamp device comprises
   exactly two clamp arms, which are provided as separate elements, wherein the clamp arms are coupled or are able to be coupled at their proximal ends to each other such that the clamp arms can be rotated around a common pivot axis, and wherein each of the clamp arms is provided with a guide groove and guide grooves of the clamp arms partially overlap each other, and
   a guide pin, which is attached to the clamp housing and extends through the guide grooves in overlapping parts of the guide grooves, so that by an engagement of the guide pin and the guide grooves a movement of the pivot axis is translated into a closing movement of the clamp arms or into an opening movement of the clamp arms around the pivot axis,
      wherein holdings humps are provided on the clamp arms, with the holding humps extending into the guide grooves from lateral sides thereof, and the guide pin comprises a radially deformable middle section extending through the guide grooves, thereby allowing the guide pin to pass the holding humps.

7. The clamp device according to claim 6, wherein the guide pin is, at least in its middle section extending through the guide grooves of the clamp arms, over its entire length, tubular shaped having an inner opening.

8. The clamp device according to claim 7, wherein at least one slit, is formed in the middle section of the guide pin.

9. The clamp device according to claim 8, wherein a plurality of slits extend in a longitudinal direction of the guide pin and/or are spaced over an entire circumference of the guide pin.

10. The clamp device according to claim 8, wherein at least one slit is formed helically over the middle section of the guide pin.

11. The clamp device according to claim 6, wherein the guide grooves have a straight, axially extending distal end section, in which the guide pin is able to move without incurring rotation of the clamp arms and the holding humps extend to the straight distal end sections, wherein each of the clamp arms has two holding humps, one holding hump of which extends from each lateral side of the guide groove.

12. The clamp device according to claim 1,
    wherein each of the clamp arms defines at its distal end a grasping section in order to grasp a tissue when the clamp device is released inside a body of a patient,
    wherein each of the clamp arms comprises two barbs arranged on laterally opposite sides of the clamp arm in the grasping section, wherein the barbs are formed such that each of the barbs points in a direction of a corresponding, opposite barb of the other clamp arm.

13. The clamp device according to claim 12, wherein a clamping contour is provided at each of the barbs at its end pointing to the corresponding, opposite barb of the other clamp arm.

14. The clamp device according to claim 13, wherein the clamping contour of each of the barbs is complementary to a clamping contour of the corresponding, opposite barb of the other clamp arm.

15. The clamp device according to claim 14, wherein the clamping contour of at least one barb comprises a V-shaped protrusion, wherein the corresponding, opposite barb of the other clamp arm has a complementary V-shaped recess.

16. The clamp device according to claim 15, wherein corners of the V-shaped protrusion(s) and/or corners of the V-shaped recess(es) are rounded.

17. The clamp device according to claim 12, wherein each of the clamp arms has one barb, a clamping contour of which comprises a V-shaped protrusion, and one barb, a clamping contour of which comprises a V-shaped recess.

18. The clamp device according to claim 12, wherein the barbs are arranged close to a distal end of the grasping section, and/or notches are formed in the clamp arms adjacent to the barbs.

19. The clamp device according to claim 12, wherein each of the clamp arms is bent inwardly towards an opposite clamp arm at its lateral edges at least over a part of the grasping section.

20. The clamp device according to claim 12, wherein a distal end of the grasping section of each of the clamp arms is bent inwards towards the other clamp arm.

21. The clamp device according to claim 20, wherein an engagement contour is formed at a distal end of each of the clamp arms, wherein engagement contours of the clamp arms are complementary to each other so that they can engage with each other when the clamp arms are closed.

22. The clamp device according to claim 21, wherein each of the engagement contours of the clamp arms comprise a corrugated profile, a sinusoidal profile or a zigzag profile.

23. The clamp device according to claim 12, wherein at least one clamp arm comprises a through-opening formed in the grasping section extending in a longitudinal direction of the clamp arm.

24. A medical device for tissue hemostasis or closure, the medical device comprising:
　a handle;
　a sheath device, which is attached to the handle;
　the clamp device according to claim 1;
　a control wire, extending through the sheath device and reversibly moveable in distal and proximal directions; and
　an actuator, coupled to a proximal end of the control wire and being actuable to reversibly move the control wire in the distal and proximal directions,
　wherein the clamp arms are each coupled to a distal end of the control wire and wherein the clamp device is actuable to open and close the clamp arms by a movement of the control wire such that a movement of the control wire in the proximal direction is translated into a closing movement of the clamp arms and a movement of the control wire in the distal direction is translated into an opening movement of the clamp arms.

* * * * *